United States Patent [19]

Gaffar et al.

[11] Patent Number: 4,514,382
[45] Date of Patent: Apr. 30, 1985

[54] ORAL PRODUCT FOR CONTROLLING GINGIVITIS

[75] Inventors: Abdul Gaffar, Somerset; Calvin B. Davis, Newark; Margita L. Vasers, Piscataway, all of N.J.

[73] Assignee: Colgate-Palmolive Company, New York, N.Y.

[21] Appl. No.: 570,446

[22] Filed: Jan. 16, 1984

Related U.S. Application Data

[63] Continuation of Ser. No. 442,405, Nov. 17, 1982, abandoned.

[51] Int. Cl.³ .............................. A61K 7/22; A61K 7/16
[52] U.S. Cl. .......................................... 424/54; 424/49
[58] Field of Search .......................................... 424/54

[56] References Cited

U.S. PATENT DOCUMENTS

| | | | |
|---|---|---|---|
| 3,497,591 | 2/1970 | Yankell et al. | 424/54 |
| 3,523,154 | 8/1970 | Gould | 424/52 |
| 3,577,520 | 5/1971 | Savini | 424/54 |
| 3,812,142 | 5/1974 | Meiser et al. | 260/309 |
| 3,903,287 | 9/1975 | Meiser et al. | 424/273 |
| 3,911,133 | 10/1975 | Edwards | 424/273 |
| 4,029,760 | 6/1977 | De Roeck et al. | 424/48 |
| 4,243,670 | 1/1981 | Regel et al. | 424/269 |
| 4,272,512 | 6/1981 | Gaffar | 424/49 |
| 4,273,758 | 6/1981 | Liau | 424/49 |

FOREIGN PATENT DOCUMENTS

| | | |
|---|---|---|
| 2430039 | 1/1976 | Fed. Rep. of Germany . |
| 2600800 | 7/1977 | Fed. Rep. of Germany . |
| 2700806 | 7/1978 | Fed. Rep. of Germany . |
| 1502144 | 5/1975 | United Kingdom . |

OTHER PUBLICATIONS

Heijl and Lindhe, J. Clinical Periodontology 6, 197–209, (1979).
Listgarton et al., J. Periodont. Res. 14: 65–75, (1979).
Loesche et al., J. Clinical Periodontology, 8: 29–44, (1981).
Flagyl, Physician Reference Handbook, p. 1761.

*Primary Examiner*—Shep K. Rose
*Attorney, Agent, or Firm*—Robert L. Stone; Murray M. Grill; Herbert S. Sylvester

[57] ABSTRACT

An oral composition for treating gingivitis and periodontitis comprising an oral vehicle and an effective amount of the water insoluble antigingivitis agent, imidazolyl-1-1-(p-chlorophenoxy) 3-3-dimethyl 2-butanone solubilized in a nonionic compound containing a mixture of hydrophobic and hydrophilic groups of sufficient length to effect solubilization in an aqueous vehicle, in the weight ratio of 1:1 to 25:1 and preferably 3:1 to 25:1 solubilizer:imidazoyl compound, said agent being selectively effective against the gram negative anaerobic micro-organisms associated with periodontitis.

11 Claims, No Drawings

ORAL PRODUCT FOR CONTROLLING GINGIVITIS

This application is a continuation of application Ser. No. 442,405, filed Nov. 17, 1982, now abandoned.

BACKGROUND OF THE INVENTION

This invention relates to an antibacterial-containing oral composition which promotes oral hygiene, controls plaque formation, gingivitis and periodontitis, by the topical application to the oral cavity, of a mouthrinse or dentifrice containing an effective amount of the antigingivitis agent, 1-imidazoyl-1-(p-chlorophenoxy) 3,3-dimethyl 2 -butanone (Climbazole by Bayer).

Periodontitis, or pyorrhea, is a disease affecting the supporting tissues of the teeth including the gingiva, the membrane lining the sockets in which the teeth lie, and the bones surrounding the teeth. The disease may initially be associated with conditions of constant irritation of the gingiva by dental plaque, food impaction, poor dental restorations, traumatic occlusion, or chemical irritants.

The gums may be seriously harmed by deposits of dental plaque, a combination of minerals and bacteria found in the mouth. The bacteria associated with plaque can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes. The pus that forms in this process is capable of destroying gum and bone tissue. Bacteria are generally found to be present during the active stages of periodontal disease. Such organisms as anaerobic gram negatives are usually present, and are found in the purulent discharge as well as in the involved tissue, and may be absorbed into the general system through the lymphatics or venous blood stream.

The progression of the pyorrheic process usually begins with gingivitis, initiating at the margins of the gums, in which the gingiva become more tender and sensitive, and appear flabby, inflamed and swollen. Periodontal pockets become apparent, and infection takes place in these pockets. Effective control and prevention of gingivitis accordingly constitutes a desideratum for the prevention of further periodontal diseases.

A multitude of materials have been previously proposed and employed for controlling oral disease and malfunctions such as plaque, calculus, tartar, caries, halitosis, and periodontal diseases such as gingivitis and pyorrhea, but none have been entirely satisfactory. For example, oral compositions containing anti-inflammatory agents which reduce the symptoms of swelling, bleeding and inflammation associated with gingivitis, by preventing tartar formation and/or countering oral calculus, include an imidazole such as histadine or histamine as disclosed in U.S. Pat. No. 3,497,591; a dichloro-2-guanidino benzimidazole, as disclosed in U.S. Pat. No. 3,523,154; carragheenin as disclosed in U.S. Pat. No. 4,029,760; a mixture of tranexamic acid and folic acid, as disclosed in U.S. Pat. No. 4,272,512; and tannic acid, as disclosed in U.S. Pat. No. 4,273,758. All of aforesaid agents are non-antimicrobial.

U.S. Pat. No. 3,577,520 also discloses a dentifrice composition containing 5,5-diaryl-2,4-imidazolidinediones in the treatment of pyorrhea, by repairing the lesions of paradontosis.

U.S. Pat. No. 3,911,133 discloses an antibacterial composition effective against both gram positive and gram negative bacteria, comprising an imidazole derivative, which is a bis(imidazolium quaternary salt), useful in mouthwashes, toothpastes and dental gels as a method of inhibiting the formation of dental plaque or in the prevention of gingivitis.

U.S. Pat. No. 4,243,670 discloses imidazolium derivatives having strong antimicrobial activity against dermatophytes, yeasts, molds, biphase fungi and gram positive cocci; and useful as an additive to oral hygiene products such as toothpastes and mouthwashes, to avoid microbially caused infections of the mucosa of the mouth and as a prophylactic against infection.

It is also known in the art, that certain gram negative organisms such as *Bacteriodes asaccharolyticus* or *Bacteriodes gingivalis* are associated with adult periodontitis. By eliminating these and other gram negative anaerobes from the plaque accumulated on the gingival tissues, effective control and prevention of periodontal disease can be achieved.

Accordingly, it has been shown by Listgarton et al in the J. Periodont. Res. 14: 65–75 (1979), that metronidazole,

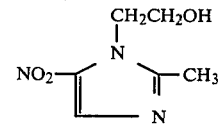

given systemically causes the elimination of said gram negative anaerobes from the plaque. This was substantiated by Heijl and Lindhe in the J. Clinical Periodontology 6, 197–209 (1979), wherein is shown that metronidazole is effective in reducing plaque and gingivitis scores in dogs; and by Loesche et al in the J. of Clinical Periodontology, 8: 29–44 (1981), wherein it is shown that metronidazole is effective in reducing the anaerobic *B. asaccharolyticus* count in plaque removed from periodontal pockets, concommitantly, with a substantial reduction in pocket depth and considerable gain in apparent attachment. However, metronidazole, sold under the tradename of Flagyl, is carcinogenic (Physician Reference Handbook p. 1761) and cannot be used indiscriminately.

It has now been found that another derivative of imidazole is effective against said gram negative anaerobic organisms, which is nonmutagenic, noncarcinogenic and can be topically applied to the oral cavity in the treatment of gingivitis, namely, 1-imidazoyl-1-(p-chlorophenoxy)3,3-dimethyl 2-butanone.

The imidazoyl ketones such as 1-imidazoyl-1-(4-chlorophenoxy)-3,3-dimethyl 2-butanone, are disclosed in U.S. Pat. Nos. 3,812,142 and 3,903,287 as an antimycotic agent, useful in pharmaceutical compositions including pastes, gels, creams, aqueous and nonaqueous suspensions. Its action against pathogenic protozoa, gram positive and negative bacteria such as Staphlococci and *Escherichia coli* is also noted therein. British Pat. No. 1,502,144 and its German counterpart, Pat. No.

2,430,039, disclose hair or skin treating compositions, effective against *Pityrosporum ovale*, containing the imidazolyl ketone antimycotic agents dispersed in a dermatologically acceptable carrier which contains a detergent-active compound. These compositions are in the form of creams, aerosols, powders and liquids. German Pat. No. 2,600,800 discloses the 1-imidazoyl-1-(4-chlorophenoxy)-3,3-dimethyl 2-butanone in a fungicidal composition, either in dry form, as a dispersion in water, water-in-oil or oil-in-water emulsion or a spray, useful for protecting plaster coatings, dispersion dyes, wallpaper, tiled surfaces, paints, glues, bitumina, furniture, leather, shower curtains, textiles, carpets, wood and paper, against a long list of pathogenic fungi, molds and bacteria. However, there is no mention of *Bacteroides asaccharolyticus* or *gingivalis*, the particular anaerobic gram negative organisms found in gingivitis. German Pat. No. 2,700,806 also discloses a mixture of the imidazolyl ketone fungicide and a quaternary ammonium bactericide useful for protecting materials such as paints, glues, bitumen, cellulose, paper, textiles, leather and wood.

Although the prior art discloses the specified imidazolyl ketone as an antimycotic agent, and its use in pharmaceutical formulations, particularly in hair and skin treating compositions, there is no disclosure of its use in dental preparations nor its effectiveness against the specific gram negative anaerobic organisms associated with gingivitis and periodontitis.

DESCRIPTION OF THE INVENTION

It has now been found that the water insoluble imidazoyl ketone, 1-imidazolyl-1-(p-chlorophenoxy)3-3-dimethyl 2-butanone, is selectively effective against the specific anaerobic gram negative organisms associated with gingivitis, when topically applied to the affected gingiva.

Accordingly, it is a primary object of the present invention to provide an oral formulation containing aforesaid water insoluble imidazolyl ketone as the antigingivitis agent solubilized in an oral vehicle.

Another object of this invention is to provide a mouthrinse or dentifrice effective in the control and treatment of plaque, gingivitis and periodontitis.

Still another object of this invention is to provide an oral composition comprising aforesaid antigingivitis agent solubilized in an aqueous vehicle comprising a nonionic compound.

Another object of this invention is to provide an antibacterial-containing oral composition useful in the prevention and treatment of gingivitis in animals.

Still another object of this invention is to provide a method of improving oral hygiene by topically applying to the oral cavity the antibacterial-containing composition comprising aforesaid solubilized imidazoyl ketone.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, this invention relates to an oral composition for controlling gingivitis comprising an oral vehicle and an effective amount of the water insoluble antigingivitis agent, 1-imidazolyl-1-(p-chlorophenoxy)3-3-dimethyl 2-butanone solubilized in a nonionic compound containing a hydrophobic radical and about 10 to 80% by weight of hydrophilic units of polyoxyethylene of sufficient length to solubilize said imidazoyl compound in an aqueous medium.

More specifically, the present invention relates to oral compositions comprising about 0.1 to 5% by weight of said antigingivitis agent, solubilized in an aqueous oral vehicle comprising a nonionic compound containing a hydrophobic radical including a higher fatty acid radical containing 10–20 carbons, polyoxypropylene, hexitan mono-higher fatty acid esters, and fatty acid amides; and the hydrophilic group polyoxyethylene of sufficient length to effect solubilization. The oral vehicle may be liquid such as a mouthwash or rinse, solid such as chewing gum, or tooth powder, pasty or creamy such as a toothpaste or dental cream. These oral compositions are nontoxic and have a pH of about 5 to 7.5.

The mouthwash which has a pH of about 5 to 7.5 is an aqueous-alcohol vehicle containing about 1–5% by weight of a nonionic surfactant selected from the group consisting of block polymers of ethylene oxide, mixed polymers of propylene oxide and ethylene oxide, polyoxyethylene hexitan mono-higher fatty acid esters containing 10–80 moles ethylene oxide per mol, and higher fatty acid mono- and di-ethanolamides and mixtures thereof.

The typical surfactant contains at least 10–80% by weight of hydrophilic units of polyoxyethylene and the hydrophobic radical such as polyoxypropylene which preferably has a molecular weight of about 3250, as in the mixed polymers of propylene oxide and ethylene oxide. The ratio of solubilizer to imidazole compound is about 1:1 to 25:1 and preferably about 3:1 to 25:1. At ratios above 25:1, gelation occurs.

The toothpaste, which also has a pH of about 5–7.5 comprises a dentally acceptable polishing material, and a liquid vehicle containing water and about 20–40% by weight of a nonionic humectant including at least one humectant selected from the group consisting of polyethylene glycol and polypropylene glycol. Glycerine, sorbitol or mannitol may be substituted for part of the humectant content provided said antigingivitis agent has been solubilized.

The antigingivitis agent utilized in present invention is 1-imidazoyl-(p-chlorophenoxy)3-3-dimethyl 2-butanone having the structural formula:

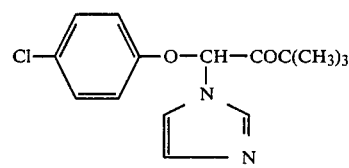

which is prepared by reacting 1-bromo-1-(4-chlorophenoxy)-3,3-dimethyl-2-butanone with imidazole dissolved in acetonitrile as disclosed in U.S. Pat. Nos. 3,812,142 and 3,903,287, which is made a part of this specification. This imidazoyl ketone is a water insoluble crystalline powder having a melting point of 94.5°–97.8° C. which may be obtained from the Bayer Company as Climbazole. Due to the water insolubility of this imidazole compound, it must first be solubilized in a nonionic compound prior to the addition of ionic materials in an aqueous medium.

It has been unexpectedly found that this antibacterial compound added to oral vehicles is not only effective against the specific anaerobic organisms involved in periodontal disease, but also reduces the disease significantly when applied topically, as well as reduces the symptoms of gingivitis associated with periodontitis. The minimum inhibitory concentration (MIC) needed to kill *Bacteroides assaccharolyticus* (Forsyth strain), determined according to the procedure of Walker et al (Antimicrobial and Chemotherapy, Vol. 16, p. 452–457, 1979), is between 7.8 to 31.2 micrograms per ml. The MIC value for *B. gingivalis* is 25 micrograms per ml. The MIC value for *B. gracilis* and Fusobacterium, other gram negative organisms is greater than 50 for each; and the MIC value for the gram positive organism *Actinomyces viscosus* is 125 for the aerobic strain and 250 for the anaerobic strain. This is clearly indicative of the selectivity of the antibacterial activity of the specific imidazole compound utilized herein as the antigingivitis agent.

Evaluation of oral compositions against gingivitis, using a 0.3% Climbazole-containing mouth rinse, made in a study on 30 beagle dogs for 10 weeks, clearly shows its superior effectiveness against gingivitis. The procedure used includes the complete removal of hard and soft dental deposits, after which the dogs are kept on a soft diet for six weeks to permit the development of gingivitis. The dentitions are then treated with the test solutions twice a day, 5 days a weeks, for about 15 seconds on each side of the mouth. The animals are examined and the degree of inflammation of the gingiva is scored according to a scale of 0 to 3. 0=No inflammation, 1=Mild, localized edema, and redness of gingival margin, no bleeding is elicited upon gentle finger pressure. 2=Moderate edema, and redness of gingival margin with bleeding upon gentle finger pressure. 3=Severe edema and ulceration of gingival margin and attached gingiva, and bleeding without gentle finger pressure. A placebo rinse and 0.5% metronidazole rinse were used as the negative and the positive controls respectfully. The data is summarized in Table 1.

into the gingival tissues. On the contrary, Climbazole has a bulky hydrophobic group, (p-chlorophenoxy)3-3-dimethyl 2-butanone, which provides good penetration into the tissues where the destructive process of periodontitis occurs, enabling this antibacterial to maintain an effective concentration to reduce the bacterial count of the gram negative anaerobic micro-organisms associated with this disease. In addition, metronidazole is, due to its nitro group, mutagenic, whereas Climbazole is not mutagenic in mutagenic tests, because it lacks the nitro group as can be seen by the structural formulae below:

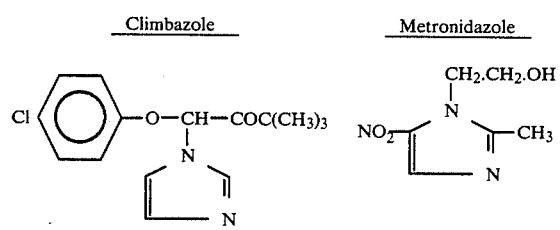

The oral composition of this invention may be liquid such as a mouthwash or rinse. In such a preparation the vehicle is typically a water-alcohol mixture. Generally, the ratio of water to alcohol is in the range of from about 1:1 to about 20:1 preferably from 3:1 to 20:1, by weight. The alcohol content preferably constitutes about 20–40% by weight of the vehicle. The total amount of water-alcohol mixture in this type of preparation is typically in the range of from about 70 to about 98% by weight of the preparation. The pH of such liquid and other preparations of the invention is generally in the range of from about 5 to about 7.5.

An essential component of the liquid oral preparations is about 1–5% by weight of a nonionic surfactant containing 10–80% by weight of hydrophilic units of polyoxyethylene and also hydrophobic polyoxypropylene or higher fatty acid, fatty ester or fatty amide, in order to solubilize the water insoluble Climbazole in the aqueous-alcohol vehicle.

Suitable nonionic surfactants include block copolymers of ethylene oxide, mixed propylene oxide-ethylene

TABLE 1

| Treatment | Initial gingival units | | | | 6 weeks | | | | 10 weeks | | | |
|---|---|---|---|---|---|---|---|---|---|---|---|---|
| | | | | | Ratings: | | | | | | | |
| | 0 | 1 | 2 | 3 | 0 | 1 | 2 | 3 | 0 | 1 | 2 | 3 |
| Placebo Rinse | 9 | 583 | 8 | — | — | 569 | 31 | — | — | 528 | 72 | — |
| 0.5% Metronidazole Rinse | 13 | 578 | 9 | — | — | 572 | 28 | — | — | 576 | 24 | — |
| 0.3% Climbazole | 11 | 589 | — | — | — | 579 | 21 | — | — | 578 | 22 | — |

Compared to the placebo, both Metronidazole and Climbazole rinses significantly reduced the development of the gingival units of 2. However, a smaller amount (0.3%) of Climbazole exhibits the same effectiveness against gingivitis than greater amounts (0.5%) of Metronidazole.

However, although metronidazole is effective against the specific gram negative micro-organisms involved in periodontal disease when used systemically, as fully discussed prior art, it does not work as well when topically applied. The reason for said poor results is due to the absence in its structural formula of an appropriate hydrophobic group which is necessary for penetration oxide polymers, polyoxyethylene hexitan mono-higher fatty acid esters having from 10–20 carbon atoms in the higher fatty acyl thereof and 4–100, preferably 10–80 mols of ethylene oxide per mol. Preferably, the hexitan is sorbitan, although mannitan and other hexitans are also often useful, the higher fatty acyl will be of 10–16 or 20 carbon atoms, more preferably of 12–16 or 18 carbon atoms and most preferably of about 12 carbon atoms, and the number of ethoxies will be from 15–80, often preferably about 20. Especially useful is an I.C.I. product sold under the tradename Tween 20, also known as Polysorbate 20 which is polyoxyethylene (20) sorbitan monolaurate.

Similarly useful products are sold under similar identifications, such as Tweens 40, 60, 65 and 80, all of which are nonionic surface active agents wherein the higher fatty acyl is palmitoyl, stearoyl or oleyoyl and the number of the mols of ethylene oxide per mol is about 20. However, of these materials the polyoxyethylene sorbitan monolaurate is usually favored. Polyoxyethylene (80) sorbitan monolaurate may be used in place of said polysorbate 20.

Other suitable nonionic surfactants include the mono- and di-ethanolamides of higher fatty acid having about 10-18 carbon atoms in the acyl group such as cocomonoethanolamide, cocodiethanolamide, lauric myristic diethanolamide, lauric monoethanolamide or combinations thereof.

Present oral compositions may be substantially pasty in character, such as a toothpaste or dental cream. The vehicle of such pasty oral preparations contains polishing material. Examples of polishing materials are water insoluble sodium metaphosphate, potassium metaphosphate, tricalcium phosphate, calcium pyrophosphate, magnesium orthophosphate, trimagnesium phosphate, calcium carbonate, alumina, hydrated alumina, aluminum silicate, zirconium silicates, silica bentonite, crystalline silica having particle sizes of up to 5 microns, silica gel, complex amorphorus alkali metal aluminosilicate, hydrated alumina, dicalcium phosphate, and mixtures thereof.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

The polishing material is generally present in amounts ranging from about 10 to about 99% by weight of the oral preparation. Preferably, it is present in amounts ranging from about 10 to about 75% in toothpaste.

In a toothpaste, the liquid vehicle comprises water and humectant typically in an amount ranging from about 10 to about 90% by weight of the preparation. An essential component of the toothpaste and dental cream is about 20-40% by weight of a nonionic humectant including at least one humectant selected from the group consisting of polyethylene glycol and polypropylene glycol in order to solubilize the water insoluble Climbazole in the aqueous vehicle. Glycerine, sorbitol or mannitol may be substituted for part of the humectant content, provided said imidazole compound is solubilized in the polyoxyethylene or polyoxypropylene glycol.

A gelling agent, such as natural or synthetic gums or gum-like materials, typically Irish moss, sodium carboxymethylcellulose, methyl cellulose, hydroxyethyl cellulose, gum tragacanth, polyvinylpyrrolidone, starch and hydroxypropyl methyl cellulose is usually present in toothpaste in an amount up to about 1% by weight, preferably in the range of from about 0.5 to about 5%. In a toothpaste or gel, the liquids and solids are proportioned to form a creamy or gelled mass which is extrudable from a pressurized container or from a collapsible, e.g., aluminum or lead, tube.

The oral compositions of this invention may contain a non-soap synthetic sufficiently water soluble organic anionic or nonionic surfactant in concentrations generally ranging from about 1-5 weight percent to promote wetting, detersive and foaming properties. U.S. Pat. No. 4,041,149 discloses such suitable anionic surfactants in col. 4, lines 31-38, and such suitable nonionic surfactants in col. 8, lines 30-68 and col. 9, lines 1-12, which passages are incorporated herein by reference thereto.

The antibacterial-containing oral compositions of this invention may optionally contain a fluorine-providing compound including inorganic fluoride salts, such as soluble alkali metal, alkaline earth metal and heavy metal salts, for example, sodium fluoride, potassium fluoride, ammonium fluoride, calcium fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type or oral preparation, but it must be a nontoxic amount. In a solid oral preparation, such as toothpaste or chewing gum, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium monofluorophosphate, the compound may be present in an amount up to 7.6% by weight, more typically about 0.76%.

Various other materials may be incorporated in the oral preparations of this invention which do not adversely affect the properties of the composition, such as sweetening agents (e.g., saccharin, sucrose, lactose, maltose, sorbitol, etc.); flavoring oils (e.g., oils of spearmint, peppermint, wintergreen, sassafras, clove, sage, eucalyptus, marjoram, cinnamon, lemon, orange, etc.), coloring or whitening agents (e.g., titanium dioxide), preservatives (e.g., sodium benzoate) and the like. Minor amounts, up to about 5% in total, and preferably 0.01 to 3% by weight of these materials may be added to the oral composition.

The present oral compositions are readily prepared by simple mixing methods from readily available components. However, it is essential that the imidazoyl compound be first mixed with the nonionic component prior to its addition to the oral vehicle which typically includes water.

For instance, a mouthrinse or mouthwash may be prepared by first solubilizing the imidazole compound by emulsifying in a nonionic surfactant prior to addition to the aqueous or alcoholic aqueous vehicle. The other ingredients such as flavor, sweetener, etc. may be added to the aqueous vehicle either prior to or subsequent to the addition of the solubilized imidazole to the aqueous vehicle.

The toothpaste may be prepared by first mixing the imidazole compound with the humectant which is nonionic, wherein it is solubilized, and then adding the thickener such as carboxymethyl cellulose to form a gel, followed by the addition of polishing agent, water and other ingredients. The sequence of the addition of the various ingredients can be varied, provided the imidazole compound is first solubilized in the nonionic humectant prior to addition to the water component.

In the practice of this invention an oral composition according to this invention such as a mouthwash or toothpaste containing 1-imidazoyl-1-(p-chlorophenoxy) 3-3-dimethyl 2-butanone antigingivitis agent in an amount effective to promore oral hygiene, is applied regularly to dental enamel, preferably from about 1 to about 3 times daily at a pH of about 5 to about 7.5.

DETAILED DESCRIPTION OF THE INVENTION

The following specific examples are further illustrative of the nature of the present invention, but it is understood that the invention is not limited thereto. All amounts and proportions referred to herein and the appended claims are by weight unless otherwise indicated.

EXAMPLE 1

Mouthrinse

| Mouthrinse solution: | |
|---|---|
| Acohol = | 25% |
| Climbazole = | 0.3% |
| Flavor (K-91-3863) = | 0.22 |
| *Pluronic F108 = | 3.0 |
| Glycerine = | 25 |
| Sodium Saccharin = | 0.03% |
| Water to make | 100% |

*Block polymer of about 80% by weight of polyoxyethylene and about 20% by weight of polyoxypropylene, the polyoxypropylene radical having a molecular weight of 3250, obtained from BASF Wyandotte Company.

The Climbazole is mixed with Pluronic until homogeneous and clear, prior to addition to the aqueous-alcoholic vehicle containing glycerin, flavor and sodium saccharin.

The resultant product is effective in controlling gingivitis and treating periodontitis, and provides a simple means of improving oral hygiene, when used on a regular regime of 1 to 3 applications to the oral cavity per day.

The unexpected superior antigingival activity of this product is shown in Table 1, wherein the mouthrinse of Example 1 was used as the test solution. This product also possesses antibacterial properties against *Bacteroides assaccharolyticus* and *B. gingivalis.*

EXAMPLE 2

Dental Paste

| Ingredients | Percent | Grams |
|---|---|---|
| H₂O | 31.3 | 156.5 |
| Na - Benzoate | 0.5 | 2.5 |
| Na - Saccharin | 0.2 | 1.0 |
| Polyethylene glycol 600¹ | 25.0 | 125 |
| Climbazole | 1.0 | 5.0 |
| Carboxymethyl cellulose | 1.5 | 7.5 |
| Syloid-244² | 3.0 | 15.0 |
| Zeo-49³ | 35.0 | 175 |
| Sodium lauryl sulfate | 1.5 | 7.5 |

| -continued | | |
|---|---|---|
| Ingredients | Percent | Grams |
| Flavor | 1.0 | 5.0 |

¹H(OCH₂CH₂)ₙOH where n is an integer between 10-14, preferably 12.5 to 14 and having a mol weight of 570–630
²colloidal silica
³sodium aluminosilicate (silica with 1% combined alumina) by Huber Co.

The Climbazole is premixed with the polyethylene glycol prior to the addition of the carboxymethyl cellulose, whereby a gel is formed. To this gel is added, with agitation, the Syloid, Zeo, sodium lauryl sulfate, flavor, water, benzoate and saccharin. The benzoate and saccharin may be dissolved in the water prior to mixing with the rest of the ingredients. Similarly, the Zeo, flavor and sodium lauryl sulfate may be premixed prior to addition to the gel.

This product also possesses similarly good antimicrobial and antigingivitis properties.

Other conventional components may be substituted or added, as disclosed hereinbefore. For example, hydrated alumina or water insoluble metaphosphate or dicalcium phosphate dihydrate and other polishing agents may be substituted for the alkali metal aluminosilicate (Zeo) or the colloidal silica (Syloid) in total or in part. Similarly, other nonionic surfactants may be substituted for the block polymer of propylene oxide and ethylene oxide (Pluronic) such as the polyoxyethylene hexitan mono-higher fatty acid esters.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. An oral composition, which is a mouthwash having a pH of about 5 to 7.5, for treating gingivitis and periodontitis comprising an oral vehicle and an effective amount, which is about 0.1–5% by weight, of the water insoluble antigingivitis agent, 1-imidazoyl-1-(p-chlorophenoxy)3-3-dimethyl 2-butanone, solubilized in a nonionic compound containing a hydrophobic radical and about 10–80% by weight of hydrophilic units of polyoxyethylene of sufficient length to effect solubilization, in the weight ratio of 3:1 to 25:1 nonionic; antigingivitis agent, said agent being selectively effective against the gram negative anaerobic microorganisms *Bacteriodes assaccharolyticus*, *Bacteriodes gingivalis* and mixtures thereof.

2. An oral composition according to claim 1, wherein the nonionic compound contains a hydrophobic poloxypropylene radical and hydrophilic polyoxyethylene radicals of sufficient length to effect subsequent solubilization in an aqueous vehicle, the weight ratio of hydrophilic:hydrophobic radicals in the nonionic compound being about 4:1.

3. The oral composition according to claim 1 having an aqueous-alcohol vehicle containing a nonionic surfactant, as the nonionic solubilizer for said antigingivitis agent, selected from the group consisting of block polymers of propylene oxide and ethylene oxide, polyoxyethylene hexitan mono-higher fatty acid esters containing 10–80 moles ethylene oxide per mol, and mixtures thereof.

4. An oral composition, which is a toothpaste having a pH of about 5 to 7.5, for treating gingivitis and periodontitis containing a dentally acceptable polishing material, a liquid vehicle comprising water and an effective amount, which is about 0.1–5% by weight, of the water insoluble antigingivitis agent, 1-imidazoyl-1-(p-chlorophenoxy)3-3-dimethyl 2-butanone, solubilized in about 20–40% by weight of the composition of a nonionic humectant including at least one humectant selected from the group consisting of polyoxyethylene glycol and polyoxypropylene glycol in the weight ratio of 3:1 to 25:1 nonionic:antigingivitis agent, said agent being selectively effective against the gram negative anaerobic microorganisms *Bacteriodes assaccharolyticus, Bacteriodes gingivalis* and mixtures thereof.

5. The oral composition according to claim 4, wherein glycerin, sorbitol or mannitol may be substituted for part of the humectant content, which constitutes about 20–40% by weight of the composition, provided said antigingivitis agent has been solubilized.

6. A method of improving oral hygiene by controlling periodontitis and gingivitis by treating periodontitis and controlling gingivitis which comprises the topical application to the oral cavity, on a daily basis, of an oral composition as defined in claim 1.

7. A method of treating gingivitis which comprises the daily application of the mouthrinse defined in claim 5 to the affected gingiva.

8. A method of controlling gingivitis which comprises the daily brushing of the teeth with the toothpaste defined in claim 4.

9. A method of controlling periodontitis and gingivitis which comprises topically applying the oral composition defined in claim 2 to the oral cavity, on a daily basis.

10. A method of controlling periodontitis and gingivitis which comprises the daily brushing of the teeth with the toothpaste defined in claim 5.

11. A method of controlling periodontitis and gingivitis which comprises the topical application to the oral cavity, on a regular basis, of an oral composition comprising an oral vehicle and an effective amount within the range of about 0.1 to about 5% by weight of the water insoluble antigingivitis agent, 1-imidazoyl-1-(p-chlorophenoxy)3-3-dimethyl 2-butanone, said agent being selectively effective against the gram negative anaerobic microorganisms *Bacteriodes assacharolyticus, Bacteriods gingivalis* and mixtures thereof.

* * * * *